United States Patent [19]

Cobb

[11] Patent Number: 5,358,508

[45] Date of Patent: Oct. 25, 1994

[54] LAPAROSCOPIC DEVICE

[76] Inventors: Eric Cobb; Henri F. de Guillebon, both of c/o Microline, Inc., 199 Newbury St., Danvers, Mass. 01923

[21] Appl. No.: 121,694

[22] Filed: Sep. 15, 1993

[51] Int. Cl.5 ............................................. A61B 17/32
[52] U.S. Cl. ..................................... 606/174; 606/170
[58] Field of Search .................. 606/51, 52, 142, 170, 606/174, 205, 206, 207, 208, 209, 210, 211, 46; 128/750–755; 30/251

[56] References Cited

U.S. PATENT DOCUMENTS

| | | | |
|---|---|---|---|
| 2,790,437 | 4/1957 | Moore | 128/751 |
| 3,404,677 | 10/1968 | Springer | 128/751 |
| 4,887,612 | 12/1989 | Esser et al. | 606/174 |
| 5,147,357 | 9/1992 | Rose et al. | 606/51 |
| 5,171,256 | 12/1992 | Smith et al. | 606/174 |
| 5,211,655 | 5/1993 | Hasson | 128/751 |

Primary Examiner—Stephen C. Pellegrino
Assistant Examiner—William W. Lewis

[57] ABSTRACT

A laparoscopic instrument assembly having a removable tip attachable to an actuator, the actuator being provided with an actuator rod disposed for axial movement within a tubular sheath. The removable tip has a pair of blades forming a scissors which are moved between an open position and a closed position by axial movement of a tip rod disposed within a tubular tip casing structure. The tip rod is threaded to the actuator rod and the tip casing structure is threaded to the actuator tubular sheath, and a pair of thumb and finger grips serve to move the actuator rod within the tubular sheath.

19 Claims, 4 Drawing Sheets

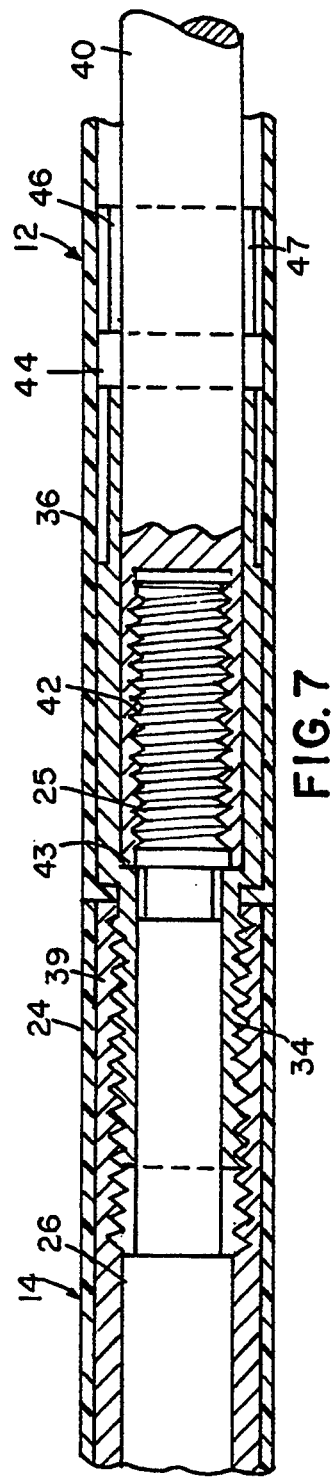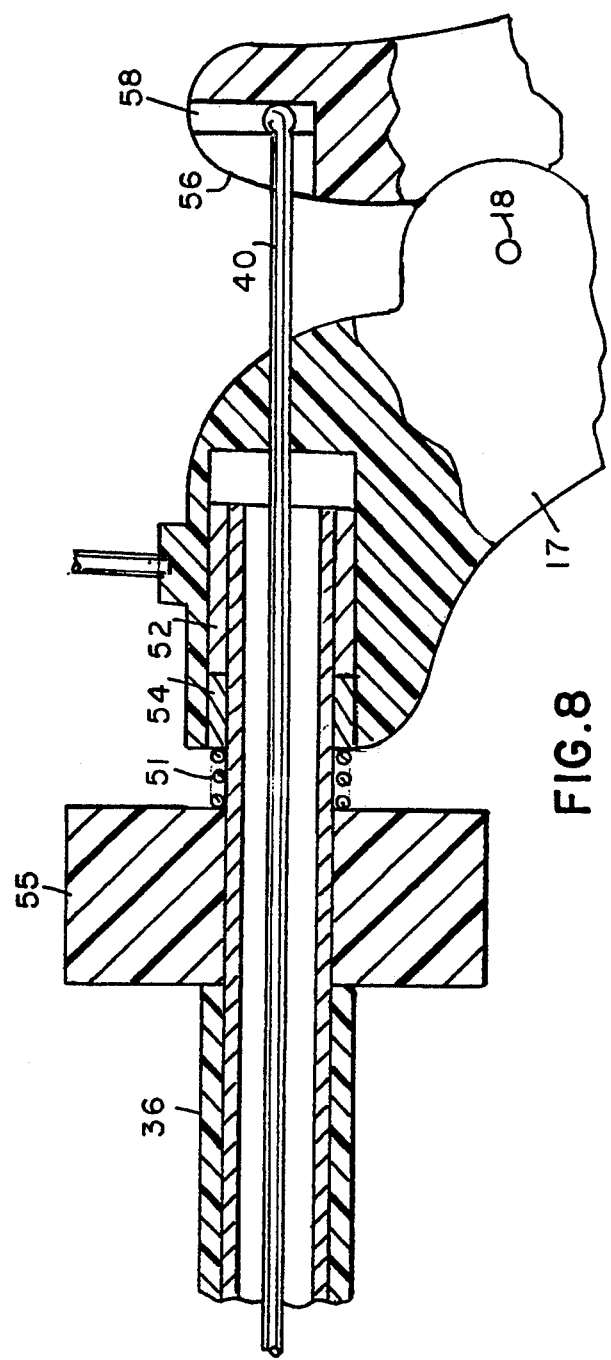

LAPAROSCOPIC DEVICE

BACKGROUND OF THE INVENTION

The present invention relates to a laparoscopic instrument and more particularly to a laparoscopic instrument having an operable tip which is disposable, and/or replaceable, the tip comprising a set of cutting blades, forceps, or the like the operation of which is controlled and actuated manually.

A wide variety of instruments are presently known which are employed in the art of laparoscopic surgery, that is a species of endoscopic surgery which involves accessing a patient's peritoneal cavity by way of an endoscope passing through the patient's abdominal wall. Such medical instruments may take the form of cutting blades, forceps or other devices wherein the device is passed through a discrete opening providing access to the patient's organs, which opening may either be surgically created or naturally occurring. In such devices the surgeon must be able to manipulate adequately the internally disposed end of the laparoscopic instrument to perform the required surgical routine. Such devices therefore are often designed such that a movable rod may be manipulated at the rear, or operative end of the instrument to manipulate the instrument whether it be forceps, scissor-type blades or the like at the forward end of the laparoscopic device.

It has been found that in particular medical instruments, such as those employing cutting blades, it is necessary to replace the blades by new and sharper blades in which case it is economically feasible to merely remove the tip of the instrument and replace it with a new tip, rather than discarding the entire instrument.

In a device which is rod actuated as discussed above, a rod portion of the newly replaced tip must essentially be connected to a mating rod of the actuator, and the outer shell of the actuator upon which the tip is to be assembled attached to the tip shell in such relation that proper movement of the instrument occurs, with movement of the rod assembly within the actuator shell, or outer casing. It has been found expedient to employ a thread engagement between the actuator rod and the tip rod as well as a thread engagement between the outer shells or casings of the tip and actuator body to ensure a positive attachment of both outer casing and rod arrangements to permit operation of the instrument in the proper manner with the new tip. It is also essential that the removal and replacement of a tip require no special mechanical knowledge or capability on the part of the operator of the instrument, and that it may be done quickly and with a high degree of reliability.

In an arrangement as set forth above a problem arises in the initial engagement of the first threads in beginning the attachment of the new tip to the instrument. Normally, one would attempt to design such engagement by precise entering of the thread alignment both axial and angular such that the first entering threads both on the rod and shell attachment start exactly together, and once engaged would proceed threading one on the other to complete the attachment. However, this procedure has found to be both expensive and require a great deal of precision in design.

It is therefore an object of the present invention to provide a laparoscopic instrument assembly having a disposable tip wherein a tip rod is disposed for axial movement within a tubular tip casing structure, the tip rod and casing structure containing threads for attachment, in which the attachment is simple in construction and inexpensive to produce.

A further object of the invention is to provide a laparoscopic instrument assembly of the type described above wherein a precise angular and axial alignment is unnecessary when assembling the tip onto the instrument assembly.

Another object of the invention is to provide a laparoscopic instrument assembly of the type described wherein a replaceable tip is easily and quickly assembled onto the instrument assembly without requiring special instructions to the user.

SUMMARY OF THE INVENTION

The above objects and other objectives which will become apparent as the description proceeds are achieved by providing a laparoscopic instrument assembly having a disposable tip, the assembly including an actuator having a tubular sheath structure with an actuator rod disposed for axial movement within the sheath. A handle is provided for moving the actuator rod axially within the sheath and is disposed adjacent the rear end of the actuator rod, the rod having a continuous internal thread formed at the forward end of the rod opposite the one end, and the sheath structure having a continuous external thread formed thereon adjacent the rod forward end.

A removable and replaceable tip is provided in the laparoscopic instrument assembly, the tip comprising a tip rod disposed for axial movement within a tubular casing structure, the tip rod having a plurality of external threads formed on the rear end thereof for mating engagement with the actuator rod's internal threads, and the tip casing structure having a plurality of internal threads at the rear end adjacent the one end of the tip rod for mating engagement with the external threads of the sheath structure. The external thread on the tip rod locates the external thread on the actuator rod and the external threads on the sheath structure locates the thread on the tip casing. The threads are spaced from each other by predetermined distances. One predetermined distance is always greater than the other predetermined distance whereby assembly of the replaceable tip on the actuator means is accomplished by the threading of the tip rod into the actuating rod prior to the threading of the sheath structure into the tip casing structure. In this way the tip can be threaded on to the actuator rod with the medical instrument in a predetermined operative position, e.g. with cutting blades closed and held together. The medical instrument disposed at the forward end of the tip casing structure is thus operated by movement of the tip rod within the tip casing structure.

The assembly generally includes a means for retaining the tip rod in its rearwardmost position during assembly of the tip rod onto the actuator means. Further, the instrument may comprise a pair of cutting blades forming a scissors.

When the instrument comprises a pair of cutting blades forming a scissors, the blades are movable to an open position with the movable tip rod in a forward position and to a closed position with the moveable tip rod in its rearwardmost position. The means for retaining the tip rod in its rearwardmost position may be provided by a tubular element slidable over the blades to retain the blades in the closed position and thereby retain the tip rod in its rearwardmost position. The movement of the blades is controlled by finger actuated grip members, one of which moves the actuator rod. Movement of the blades beyond a predetermined point of closure is controlled by a stop on one of the handles that prevents over closure and also aligns the blades so when the tip is threaded on the actuator rod and sheath, the blades will be properly disposed relative to each other and also the threads on the end of the actuator rod will be at the correct position to receive the threads on the end of the replaceable tip.

In another aspect of the invention, with a pair of cutting blades forming a scissors, the cutting blades may be movable to an open and closed position by rotation about a pivot pin retained in the tubular tip casing structure, each of the cutting blades having a slotted opening formed therein rearwardly of the pivot pin, the slotted openings forming an acute angle one with the other. A yoke having a pair of forwardly extending arms is formed at the forward end of the tip rod and has a driving pin disposed between the yoke arms and extending through the blade slots whereby axial movement of the tip rod is effective to move the yoke and the driving pin in the blade slots causing the blades to move between closed and open positions.

The means for moving the actuator rod axially within the sheath may comprise a pair of thumb and finger grip members one fixed at the rear end of the sheath and the other pivotally attached to a point adjacent the sheath. The other pivotal grip member is then interconnected to the rear end of the actuator rod extending beyond the sheath and movement of the grip members toward and away from one another is effective to move the actuator rod within the sheath due to pivotal movement of the grip member about the pivotable attachment.

In construction of the sheath structure the sheath structure at its forward end may be made comprising a tubular member having a metallic insert disposed within its forward end, the metallic insert having a continuous external thread formed thereon at the forward end thereof and an elongated slot formed on the rear end thereof extending axially with respect to the actuator rod. An actuator rod pin in this instance extends outwardly from the surface of the actuator rod into the slot whereby rotation of the actuator rod is inhibited during assembly of the replaceable tip onto the actuator means.

The assembly may further include a means for rotating the actuator sheath relative to the means for moving the actuator rod axially within the sheath.

BRIEF DESCRIPTION OF THE DRAWING

Reference is made to the accompanying drawing in which there is shown an illustrative embodiment of the invention from which its novel features and advantages will be apparent, wherein:

FIG. 7 is a fragmentary sectional view similar to FIG. 6 showing the structure of FIG. 6 with the tip in an operative position; and FIG. 8 is an elevational fragmentary sectional view showing features of a portion of the structure of FIG. 1 taken on an enlarged scale for clarity.

DESCRIPTION OF THE PREFERRED EMBODIMENT

Figure 1:
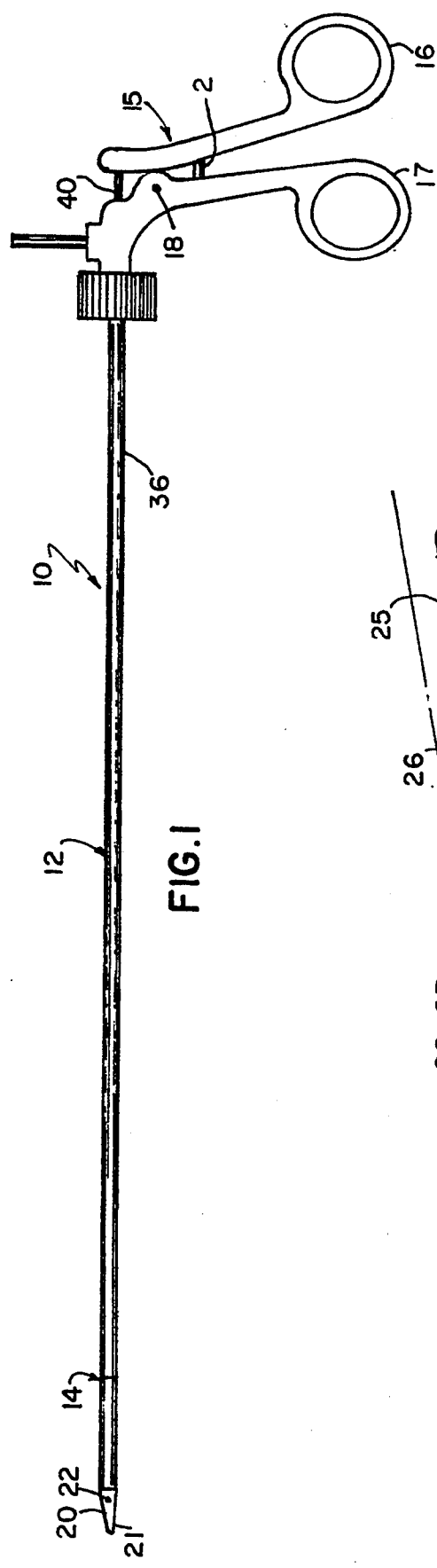
FIG. 1 is a side elevational view showing a laparoscopic instrument assembly constructed in accordance with the teachings of the present invention.

Referring now to the drawing and in particular to FIGS. 1 through 4 there is shown a laparoscopic instrument assembly 10 comprising an actuator 12 and an operable tip 14 the operable tip being removable and replaceable onto the actuator 12. The actuator 12 is provided with a handle 15 comprising a pair of thumb and finger grip members 16 and 17 respectively, the finger grip member 17 being stationary with respect to the actuator 12 while the thumb grip member 16 is movable through rotation about a pivot pin 18. A stop 2 on grip 16 sets the position of the blades so that they are completely closed when it engages grip 17 and also establishes the correct position for the threads on the tip to engage the threads on the actuator.

Figure 2:
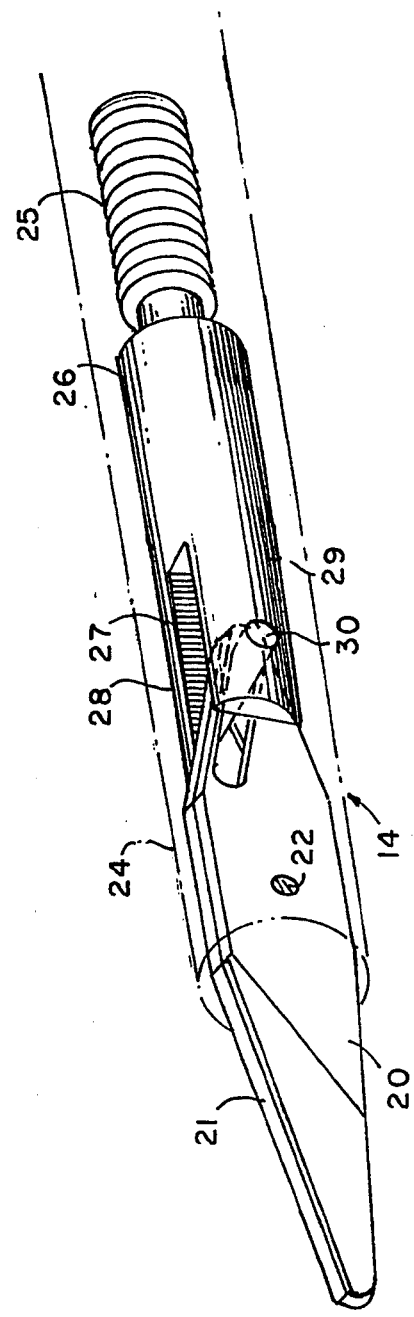
FIG. 2 is a perspective elevational view showing a removable and disposable tip which is part of the assembly of FIG. 1, taken on an enlarged scale for clarity.
Figure 3:
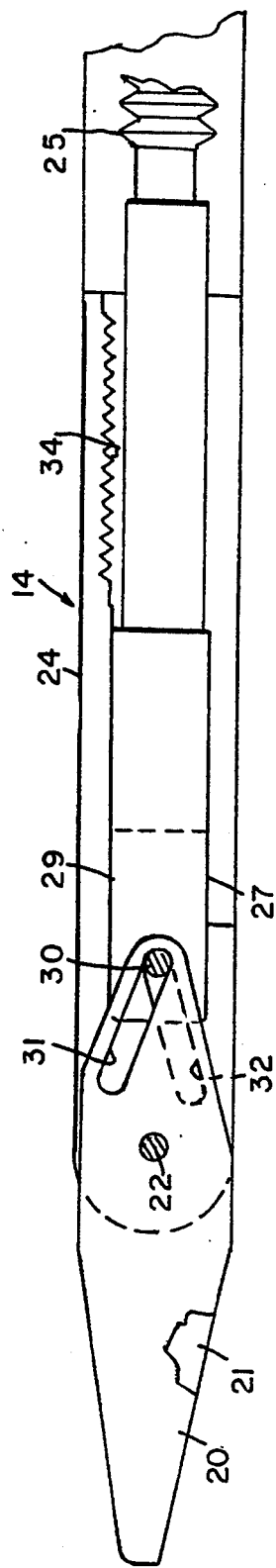
FIG. 3 is an elevational view, partially in section, showing features of the tip of FIG. 2 when in the assembly, taken on an enlarged scale.
Figure 4:
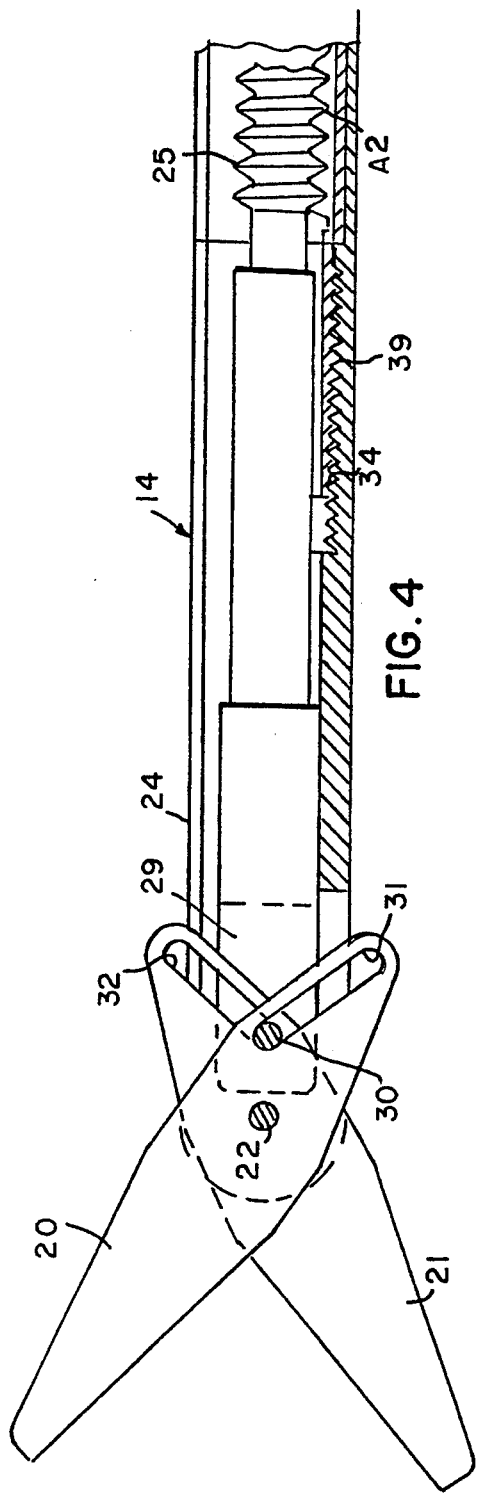
FIG. 4 is an elevational view, partially in section, similar to FIG. 3, showing the tip in a second operative position.

At the forward end of the assembly 10 the instrument employed in the assembly is shown to comprise a pair of cutting blades 20 and 21 forming a scissors the blades being movable to an open and closed position by rotation about a pivot pin 22 as best shown in FIGS. 2 through 4.

Referring still to FIGS. 2 through 4 the operable tip 14 is shown to include a tubular tip casing structure 24 in which the blades 20, 21 are disposed, the pivot pin 22 extending through each of the blades and being affixed to the wall of the casing structure.

At the rear of the casing structure 24 a tip rod 26 is located having an external thread 25 formed on the rear end thereof, and a yoke 27 extending forwardly from the tip rod 26. The yoke 27 comprises a pair of arms 28 and 29 having blades 20 and 21 disposed therebetween and a drive pin 30 is affixed between the arms 28 and 29. Each of the blades 20, 21 has a slotted opening 31 and 32 respectively formed at the rear of the pin 22, each forming an acute angle one with the other and having the drive pin 30 received in the slotted openings.

The tip rod 26 is slidable within the casing structure 24 and is effective to cause the blades 20 and 21 to move to an open position with the movable tip rod 26 in a forward position and to a closed position with the movable tip rod in its rearwardmost position, as best shown in FIGS. 3 and 4.

In addition to the continuous thread 25 formed on the tip rod 26 the operable tip 14 is provided with a continuous internal thread 34 formed on the inner surface of the tip casing structure 24 as shown in FIGS. 3 and 4.

Figure 5:
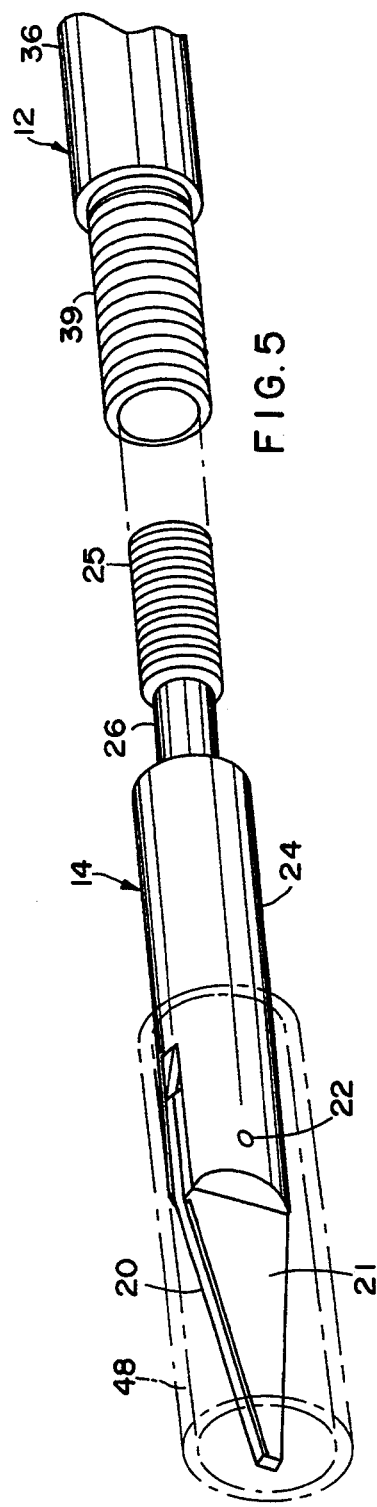
FIG. 5 is a perspective view similar to FIG. 2 showing the assembly of the tip of FIGS. 1 through 4 as it is about to be embodied into the assembly of FIG. 1.
Figure 6:
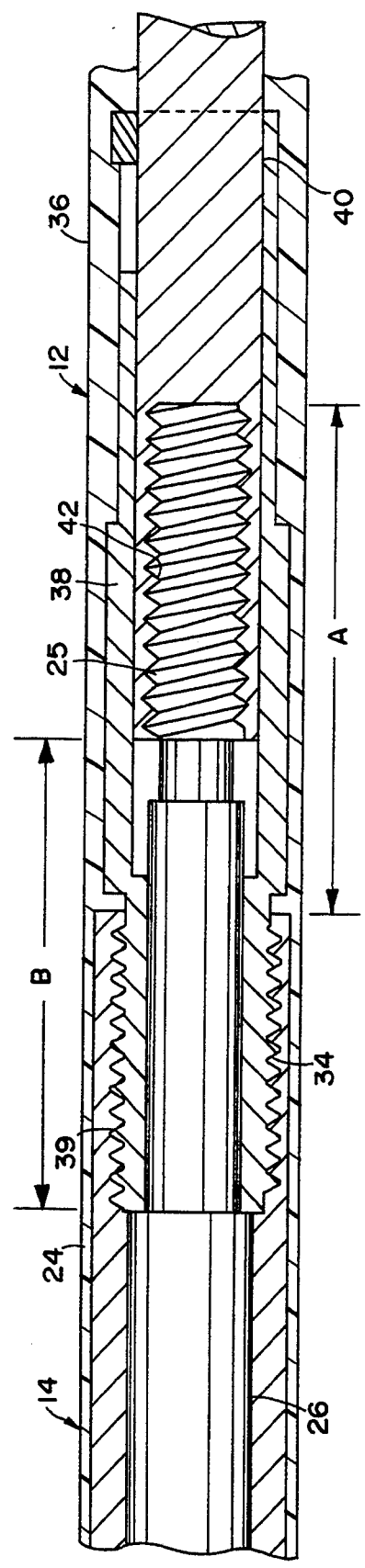
FIG. 6 is a fragmentary sectional view showing details of the structure of FIG. 5 in the initial assembled condition.

Referring now to FIGS. 5 through 7, the actuator 12 is shown to comprise a outer sheath 36 having at its forward end a metallic insert 38 which may be press fit into the sheath 36 or otherwise firmly held by the sheath against rotation, or axial movement. As shown in FIG. 5, the insert 38 has a continuous external thread 39 formed at its forward end the thread 39 being of matching pitch and diameter to the internal thread 34 provided on the operable tip 14.

An actuator rod 40 is slidably disposed within the sheath 36 extending into the insert 38 and having an internal thread 42 disposed at the forwardmost end of the actuator. The internal thread 42 is of the same diameter and pitch as the external thread 25 formed on the tip rod 26 and extends into the insert 38 to a shoulder 43 contained on the insert. As best shown in FIG. 7, the actuator rod 40 further has a draw pin 44 extending therethrough, which is received by a pair of elongated slots 46 and 47 formed at the rear end of the insert 38 to prevent rotation of the actuator 40 within the sheath 36, but to allow movement of the rod in the axial direction. The pin 44 need not extend wholly through rod 40 but can be disposed so it can slide in either slot 46 or 47.

As previously discussed, when it is necessary to replace the operable tip 14 with a new tip a problem exists in aligning the tip rod 26 with the actuator rod 40 and threading the two while also aligning the tip casing structure 24 with the sheath 36 and threading the two together. While it is possible to design the structure such that engagement is such that the entering first thread both outer and inner start exactly together by precise entering of the thread alignment both axial and angular the design of such structure would be both expensive and difficult to manipulate by the user.

In the present structure the blades 20 and 21 are maintained in the closed position which maintains the tip rod 26 and consequently the external threads 25 in their rearwardmost position. To accomplish this, means such as a removable plastic tube 48 slidable over the blades 20 and 21 which inhibits opening of the blades. As best shown in FIG. 6, with the tip rod 26 in its rearwardmost position the distance A, which is that distance between the first external thread 25 on the tip rod 26 and the first internal thread 34 on the tip casing structure 24 is constructed to be slightly greater than the distance B which is the distance between the second internal thread 42 on the actuator rod 40 and the second external thread 39 on the insert 38, with the actuator rod 40 in its forwardmost position. More threads per inch are formed, e.g. 40, on first internal thread 34 (and on first external thread 39 also) than on second internal thread 42 (and second external thread 25 also), e.g. 36. Thus the tip rod external thread 25 is engaged into the internal thread 42 of the actuator rod by one to several completed thread turns aligning the tip rod 26 with the actuator rod 40 prior to engagement of the external thread 39 of the insert 38 into the internal thread 34 of the casing structure 24. With the tip rod 26 and the actuator rod 40 in alignment and the threaded engagement started, the threads 34 and 39 are engaged and by continuing to press the new tip inwardly while continuing to turn it, full engagement is accomplished. After the assembly has taken place, the tube 48 is removed and the instrument assembly is ready for operation.

Referring now to FIGS. 1 and 8, the sheath 36 is shown to be mounted into the handle by a bushing 52. The sheath extends through a collar 54 mounted in the handle 17, the sheath being retained in place by the collar 54. A knurled knob 55 is mounted on the sheath 36 for rotation of the sheath about the handle. A spring 51 is disposed between collar 54 and knob 55 and urges bushing 52 against collar 54. The actuator rod 40 is provided with a ball at the end thereof which is retained in a slotted opening 56 having a circular cross-section 58 such that the rod may be rotated within the handle 15 to change orientation of the blades 20 and 21 during operation of the device.

From the above it will be understood that the laparoscopic instrument assembly constructed in accordance with the present invention provides a device in which the tip may be exchanged simply and without any detailed instructions by the user. Further, in operation the device may be employed in a number of orientations throughout a 360° area about the handle, is simple to use and may be manufactured inexpensively.

While it is apparent that changes and modifications can be made within the spirit and scope of the present invention, it is our intention however only to be limited by the appended claims.

As our invention we claim:

1. A laparoscopic instrument assembly having a disposable tip said assembly including:

actuator means comprising a tubular sheath structure having an actuator rod having a forward end and a rear end disposed for axial movement therein;

means disposed adjacent the rear end of said actuator rod for moving said actuator rod axially within said sheath;

said actuator rod having a continuous internal thread formed therein at the forward end thereof;

said sheath structure further having a continuous external thread formed therein adjacent said rod forward end;

replaceable tip means comprising a tip rod having a rear end disposed for axial movement within a tubular tip casing structure said tip casing having a rear end;

said tip rod having a plurality of external threads formed on the rear end thereof for mating engagement with said actuator rod internal threads; and said tip casing structure having a plurality of internal threads at the rear end adjacent said rear end of said tip rod for mating engagement with said external threads of said sheath structure;

said tip rod in its rearwardmost position locating a first thread on said tip rod a first predetermined distance from a first thread on said tip casing structure, and said actuating rod in its rearwardmost position locating a first thread on said actuating rod a second predetermined distance from said first thread on said sheath structure, said first predetermined distance being greater than said second predetermined distance;

whereby assembly of said replaceable tip on said actuator means is accomplished by the threading of said tip rod into said actuating rod prior to the threading of said sheath structure into said tip casing structure; and an instrument disposed at the forward end of said tip casing structure operative by movement of said tip rod within said tip casing structure.

2. The assembly of claim 1 which further includes means on said replaceable tip means for retaining said tip rod in its rearwardmost position.

3. The assembly of claim 1 wherein said instrument comprises a pair of cutting blades forming a scissors.

4. The assembly of claim 3 wherein said blades are movable to an open position with said movable tip rod in a forward position and to a closed position with the movable tip rod in its rearwardmost position and further includes means disposed on said cutting blades to retain said blades in the closed position and thereby retain said tip rod in the rearwardmost position.

5. The assembly of claim 4 wherein said means for retaining said blades in the closed position is a removable tubular element slidable over said blades in the closed position.

6. The assembly of claim 1 wherein said instrument comprises a pair of cutting blades forming a scissors, said cutting blades being movable to an open and closed position by rotation about a pivot pin retained in the tubular tip casing structure;

each of said cutting blades further having a slotted opening formed therein rearwardly of said pivot pin, said openings forming an acute angle one with the other;

a yoke having a pair of forwardly extending arms formed at the forward end of said tip rod having a driving pin disposed between said yoke arms and extending through said blade slots whereby axial movement of said tip rod is effective to move said yoke and said driving pin in said blade slots causing said blades to move between a closed and open position.

7. The assembly of claim 1 wherein said means for moving said actuator rod axially within said sheath comprises a pair of thumb and finger grip members, one grip member fixed at the rear end of said sheath and the other pivotally attached thereto at a point adjacent said sheath;

said other grip member being interconnected to the rear end of said actuator rod extending beyond said sheath and being effective to move said actuator rod within said sheath when rotated about said pivotal attachment.

8. The assembly according to claim 1 wherein there are less threads per inch on the actuator rod thread then on the tip rod.

9. The assembly of claim 1 wherein said sheath structure at its forward end comprises a tubular member having a metallic insert disposed within the forward end thereof;

said metallic insert having said continuous external thread formed thereon at the forward end thereof and an elongated slot formed on the rear end thereof extending axially with respect to said actuator rod; and an actuator rod pin extending outwardly from the surface of said actuator rod into said slot whereby rotation of said actuator rod is inhibited during assembly of said replaceable tip means onto said actuator means.

10. The assembly of claim 1 which further includes means for rotating said actuator sheath relative to said means for moving said actuator rod axially within said sheath.

11. The assembly of claim 2 wherein said instrument comprises a pair of cutting blades forming a scissors.

12. The assembly of claim 11 wherein said blades are movable to an open position with said movable tip rod in a forward position and to a closed position with the movable tip rod in its rearwardmost position and further includes means disposed on said cutting blades to retain said blades in the closed position and thereby retain said tip rod in the rearwardmost position.

13. The assembly of claim 12 wherein said means for retaining said blades in the closed position is a removable tubular element slidable over said blades in the closed position.

14. The assembly of claim 13 wherein said cutting blades are movable to an open and closed position by rotation about a pivot pin retained in the tubular tip casing structure;

each of said cutting blades further having a slotted opening formed therein rearwardly of said pivot pin said openings forming an acute angle one with the other;

a yoke having a pair of arms formed at the forward end of said tip rod having a driving pin disposed between said yoke arms and extending through said blade slots whereby axial movement of said tip rod is effective to move said yoke and said driving pin in said blade slots causing said blades to move between a closed and open position.

15. The assembly of claim 12 wherein said means for moving said actuator rod axially within said sheath comprises a pair of thumb and finger grip members, one grip member fixed at the rear end of said sheath and the other pivotally attached thereto at a point adjacent said sheath;

said other grip member being interconnected to the rear end of said actuator rod extending beyond said sheath and being effective to move said actuator rod within said sheath when rotated about said pivotal attachment.

16. The assembly of claim 15 wherein said sheath structure at its forward end comprises a tubular member having a metallic insert disposed within the forward end thereof;

said metallic insert having said continuous external thread formed thereon at the forward end thereof and an elongated slot formed on the rear end thereof extending axially with respect to said actuator rod; and an actuator rod pin extending outwardly from the surface of said actuator rod into said slot whereby rotation of said actuator rod is inhibited during assembly of said replaceable tip means onto said actuator means.

17. The assembly of claim 16 which further includes means for rotating said actuator sheath relative to said means for moving said actuator rod axially within said sheath.

18. A laparoscopic instrument assembly having a disposable tip assembly mounted on a tubular sheath structure having an actuator rod disposed for axial movement therein;

said tip assembly comprising a tip rod disposed for axial movement within a tubular tip casing structure;

a pair of cutting blades forming a scissors disposed at the forward end of said tip assembly;

said cutting blades being movable to an open and closed position by rotation about a pivot pin retained in said casing structure;

each of said cutting blades further having a slotted opening formed therein rearwardly of said pivot pin, said openings forming an acute angle one with the other;

a yoke having a pair of forwardly extending arms formed at the forward end of said tip rod having a driving pin disposed between said yoke arms and extending through said blade slots; and means connecting said tip rod with said actuator rod whereby movement of said actuator rod is effective to move said driving pin in said blade slots causing movement of said blades between an open and closed position.

19. The assembly of claim 18 wherein said tip rod is threaded onto said actuator rod and said tubular tip is threaded onto said tubular sheath structure.

* * * * *